US008563726B2

(12) United States Patent
Cheng et al.

(10) Patent No.: US 8,563,726 B2
(45) Date of Patent: *Oct. 22, 2013

(54) STEREOSELECTIVE REDUCTION OF A MORPHINONE

(75) Inventors: Lin Cheng, Huntsville, AL (US); Michael D. Bentley, Huntsville, AL (US)

(73) Assignee: Nektar Therapeutics, San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/447,131

(22) Filed: Apr. 13, 2012

(65) Prior Publication Data

US 2013/0018190 A1  Jan. 17, 2013

Related U.S. Application Data

(63) Continuation of application No. 12/297,632, filed as application No. PCT/US2007/009761 on Apr. 19, 2007, now Pat. No. 8,183,376.

(60) Provisional application No. 60/745,336, filed on Apr. 21, 2006.

(51) Int. Cl.
    *C07D 489/02* (2006.01)
(52) U.S. Cl.
    USPC .......................................................... 546/45
(58) Field of Classification Search
    USPC .......................................................... 546/45
    See application file for complete search history.

(56) References Cited

U.S. PATENT DOCUMENTS

| | | | |
|---|---|---|---|
| 2,628,962 A | 2/1953 | Homeyer et al. |
| 2,649,454 A | 8/1953 | Rappoport et al. |
| 2,654,756 A | 10/1953 | Homeyer et al. |
| 2,715,626 A | 8/1955 | Pfister et al. |
| 2,806,033 A | 9/1957 | Lewenstein et al. |
| 3,254,088 A | 5/1966 | Lewenstein et al. |
| 3,332,950 A | 7/1967 | Blumberg et al. |
| 3,393,197 A | 7/1968 | Pachter et al. |
| 4,089,855 A | 5/1978 | Chatterjie et al. |
| 5,240,933 A | 8/1993 | Merz et al. |
| 5,428,159 A | 6/1995 | Shieh et al. |
| 7,056,500 B2 | 6/2006 | Bentley |
| 7,662,365 B2 | 2/2010 | Bentley et al. |
| 7,786,133 B2 | 8/2010 | Bentley et al. |
| 2005/0136031 A1 | 6/2005 | Bentley et al. |
| 2006/0105046 A1 | 5/2006 | Bentley et al. |

FOREIGN PATENT DOCUMENTS

| | | |
|---|---|---|
| EP | 0846694 A1 | 6/1998 |
| WO | WO 92/22330 A1 | 12/1992 |
| WO | WO 95/32973 A1 | 12/1995 |
| WO | WO 2005/058367 A2 | 6/2005 |

OTHER PUBLICATIONS

Grant & Hackh's Chemical Dictionary (5th Ed. 1987), pp. 492-494.
Bennett et al., "Biodegradable Polymeric Prodrugs of Naltrexone," J. Controlled Release, No. 16, pp. 43-52, (1991).
Batz et al., "Pharmacologically Active Polymers 9th Report: Retard Forms of Morphine Antagonists," Drug Res., pp. 1-18, (1977).
Olde et al., Neuroscience, 15(4), 15(4) pp. 1247-1253 (1985).
Erez et al., J. Med. Chem.,25, pp. 847-849, (1982).
Guiotto et al., Bioorganic & Medicinal Chemistry, 12 pp. 5031-5037, (2004).
Greenwald et al., J. Med. Chem., No. 42, pp. 3657-3667 (1999).
Greenwald et al., J. Med Chem., No. 43, pp. 475-487, (2000).
Lenz et al., "Stereoselective Reduction of Codeinone, the Penultimate Enzymic Step During Morphine Biosynthesis in *Papaver somniferum*", Tel. Ltrs, 36(14), pp. 2449-2452 (1995).
Chatterjie et al., J. Org. Chem 41(22) pp. 3624-3625 (1976).
Davankov, "Analytical Chiral Separation Methods" Pure. Appl. Chem., 69(7), pp. 1469-1474, (1997).
Malspeis et al.,Res. Commun. Chem. Pathol. Pharmacol., 12(1), pp. 43-65, (1975).
Harris et al., Effect of Pegylation on Pharmaceuticals, Nature, 2, pp. 214-221 (2003).
ISA, International Preliminary Exam Report on Patentability corresponding to PCT/US2007/009761, dated Oct. 28,2008.
ISA, International Search Report corresponding to PCTIUS2007/009761, dated Aug. 5, 2008.
Brine et al., "Ring C Conformation of 6β-Naltrexol and 6α-Naltrexol Evidence from Proton and Carbon-13 NMR," J. Org. Chem, 41(21), pp. 3445-3448 (1976).
Chatterjie et al., "Stereospecific synthesis of the 6β-hydroxy metabolites of naltrexone and naloxone," J. Med. Chem., Am. Chemical Society, 18(5), pp. 490-492 (1975).
Hahn, et al., "Narcotic Antagonists. V. Stereochemistry of Reactions at C-6 in 14-Hydroxynoroxymorphone Derivatives," J. Org. Chem, 40(1), pp. 31-34 (1975).
Kayakiri et al., Medicinal Chemistry Research, 6 pp. 427-438(1996).
Olsen et al., J. Med. Chem., Am. Chemical Society, 33(2), pp. 737-741 (1990).
EPO, Supplementary European Search Report dated Apr. 19, 2010 for EP 07755867.

*Primary Examiner* — Jason M Nolan
(74) *Attorney, Agent, or Firm* — Jones Day

(57) ABSTRACT

A synthetic method is provided, wherein the method comprises stereoselectively reducing a ketone of a morphinone to form a reduced morphinone and optionally covalently attaching a water soluble polymer to the reduced morphinone.

8 Claims, 1 Drawing Sheet

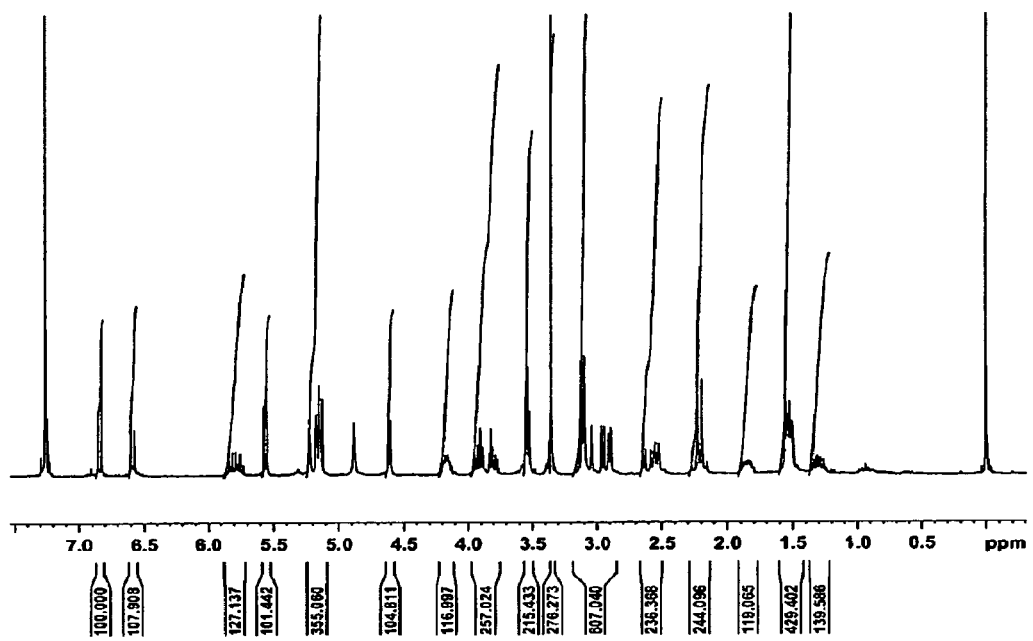
$^1$H NMR spectrum of α-6-OH-3-MEM-O-Naloxol in CDCl$_3$.

STEREOSELECTIVE REDUCTION OF A MORPHINONE

CROSS-REFERENCED TO RELATED APPLICATIONS

This application is a continuation of U.S. patent application Ser. No. 12/297,632, filed Feb. 25, 2009, now U.S. Pat. No. 8,183,376 which is a 35 USC §371 application of International Application No. PCT/US2007/009761 filed Apr. 19, 2007, designating the United States, which claims benefit of U.S. Application No. 60/745,336 filed Apr. 21, 2006, all of which are hereby incorporated by reference in their entireties.

FIELD OF THE INVENTION

One or more embodiments of the present invention relate to, among other things, chemical synthetic methods. In addition, the invention relates to (among other things) conjugates of a water-soluble polymer and active agent, compositions comprising the same, and methods of administering a conjugate.

BACKGROUND OF THE INVENTION

Conceptually, PEGylation has been described as the attachment of a poly(ethylene glycol) derivative to a pharmacologically active agent to thereby form a "conjugate." In practice, a polymeric reagent (which is a water-soluble polymer bearing a reactive functional group or an "activated" functional group) is typically reacted with an active agent of interest in order to attach or link the water-soluble polymer (either directly or through a linking moiety) to the active agent through a covalent bond. As compared to the active agent lacking attachment of the water-soluble polymer, the conjugate may possess an extended half-life in vivo, decreased immunogenicity, increased hydrophilic character, or some combination of the foregoing. Harris et al. have provided a review of the effects of PEGylation on pharmaceuticals. Harris et al. (2003) *Nat. Rev. Drug Discov.* 2(3): 214-221.

Several examples of PEGylated active agents available commercially include PEGASYS® PEGylated interferon alpha-2a (Hoffmann-La Roche, Nutley, N.J.), PEG-INTRON® PEGylated interferon alpha-2b (Schering Corp., Kennilworth, N.J.), NEULASTA™ PEG-filgrastim (Amgen Inc., Thousand Oaks, Calif.), and MACUGEN® PEGylated aptamer (Pfizer Inc., New York, N.Y.). Although each of the active agents in each of these examples is a "large molecule," small molecules such as distearoylphosphatidylethanolamine (Zalipsky (1993) *Bioconjug. Chem.* 4(4):296-299) and fluorouracil (Ouchi et al. (1992) *Drug Des. Discov.* 9(1):93-105) have also been PEGylated. Thus, many types of molecules can potentially benefit from PEGylation.

While the general benefits of PEGylation are known, attaching a poly(ethylene glycol) derivative to an active agent is often challenging and may not always be possible. For example, difficulties can be encountered when the active agent of interest does not include a chemical functional group suitable for reaction with a polymeric reagent. Further, to the extent that a suitable chemical functional group is present on the active agent of interest, the resulting conjugate may be insufficiently pharmacologically active as a result of the attached polymer interfering with, for example, a binding site necessary for activity of the active agent U.S. Patent Application Publication No. 2005/0136031 describes, among other things, a conjugate of poly(ethylene glycol) and a narcotic antagonist. In order to effect conjugation at the desired location, however, several steps must be taken. As described in this reference, the 6-keto group of 3-MEM-naloxone (a 3-hydroxy-protected naloxone) is reduced with sodium borohydride ($NaBH_4$) to form an α- and /β-epimer mixture of 6-hydroxy-3-MEM-naloxol. A polymeric reagent is thereafter covalently attached at the available hydroxyl group to thereby form an α- and β-epimer mixture of 6-polymer-3-MEM-naloxol. Once the protecting group is removed, α- and β-epimers are separated and isolated using an appropriate column. Separation and isolation of epimers is desired because, as shown in U.S. Patent Application Publication No. 2005/0136031, individual isomers of 6-polymer-3-MEM-naloxol have different properties.

Stereoselective reduction of naltrexone to α-naltrexol using tri-sec-butylborohydride has been described by Malspeis et al. Malspeis et al. (1975) *Res. Commum. Chem. Pathol. Pharmacol.* 12(1):43-65. Malspeis et al., however, does not describe stereoselective reduction of compounds other than naltrexone.

Although the approach for preparing compositions comprising substantially pure isomers of 6-polymer-3-MEM-naloxol described in U.S. Patent Application Publication No. 2005/0136031 is effective, an approach that requires fewer steps—such as eliminating the need to separate and isolate individual epimers—would be advantageous. Thus, one or more embodiments of the present invention provide, among other things, a synthetic method that eliminates the need to separate and isolate individual epimers of conjugates of poly (ethylene glycol) and a narcotic antagonist.

SUMMARY OF THE INVENTION

Accordingly, a synthetic method is provided, the synthetic method comprising stereoselectively reducing a ketone of a morphinone to form a reduced morphinone, and optionally, covalently attaching a water-soluble polymer to the reduced morphinone. Broadly, a morphinone is a phenanthrene-based moiety that (a) comprises the following structure:

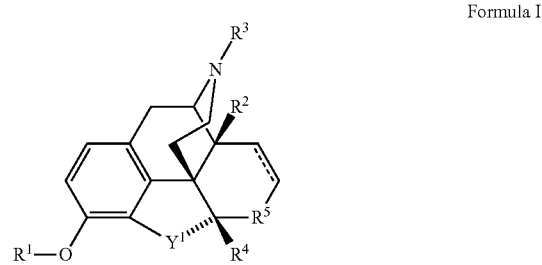

Formula I wherein:
$R^1$ is H, an organic radical, or a hydroxyl protecting group;
$R^2$ is H or OH;
$R^3$ is H or an organic radical;
$R^4$ is H or an organic radical;
the dotted line ("---") represents an optional double bond;
$Y^1$ is O or S; and
$R^5$ is selected from the group consisting of

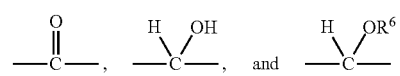

(without regard to stereochemistry), wherein $R^6$ is an organic radical; and (b) contains a ketone [either pursuant to the structure defined for the phenanthrene-based moiety provided in (a), i.e., Formula I, or by replacement of atom in the phenanthrene-based moiety provided in (a)i.e., Formula I, for a ketone]. For certain morphinones, the synthetic method of the invention includes the step of covalently attaching a water-soluble polymer to the reduced morphinone.

In one or more embodiments of the invention, a composition is provided, the composition comprising a mixture of α-epimers and β-epimers of a reduced morphinone, wherein the ratio of α-epimers and β-epimers is at least 60 to 40.

In one or more embodiments of the invention, a synthetic method is provided, the method comprising:

selectively reducing a ketone of a morphinone to form a reduced morphinone, wherein the morphinone comprises the following structure

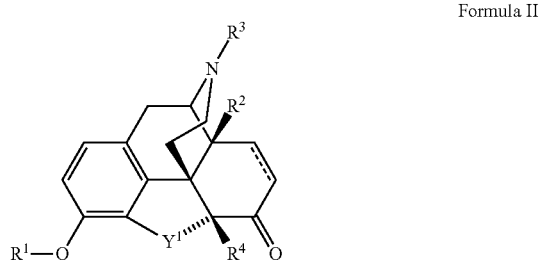

Formula II wherein:
$R^1$ is H, an organic radical, or a hydroxyl protecting group;
$R^2$ is H or OH;
$R^3$ is H or an organic radical;
$R^4$ is H or an organic radical;
the dotted line ("---") represents an optional double bond; and
$Y^1$ is O or S; and covalently attaching a water-soluble polymer to the reduced morphinone.

In one or more embodiments of the invention, a composition is provided, the composition comprising conjugates prepared by a synthetic method provided herein.

In one or more embodiments of the invention, a composition is provided, the composition comprising a conjugate as described herein in combination with a pharmaceutical excipient.

BRIEF DESCRIPTION OF THE DRAWING

FIG. 1 is an $^1$H NMR spectrum of α-6-OH-3-MEM-O-Naloxol in $CDCl_3$.

DETAILED DESCRIPTION OF THE INVENTION

Before describing one or more embodiments of the present invention in detail, it is to be understood that this invention is not limited to the particular polymers, synthetic techniques, and the like, as such may vary.

It must be noted that, as used in this specification and the intended claims, the singular forms "a," "an," and "the" include plural referents unless the context clearly dictates otherwise. Thus, for example, reference to "a polymer" includes a single polymer as well as two or more of the same or different polymers, reference to "an optional excipient" refers to a single optional excipient as well as two or more of the same or different optional excipients, and the like.

In describing and claiming one or more embodiments of the present invention, the following terminology will be used in accordance with the definitions described below.

"PEG," "polyethylene glycol" and "poly(ethylene glycol)" as used herein, are interchangeable and meant to encompass any nonpeptidic water-soluble poly(ethylene oxide). Typically, PEGs for use in accordance with the invention comprise the following structure "—$(OCH_2CH_2)_n$—" where (n) is 2 to 4000. As used herein, PEG also includes "—$CH_2CH_2$—O$(CH_2CH_2O)_n$—$CH_2CH_2$—" and "—$(OCH_2CH_2)_nO$—," depending upon whether or not the terminal oxygens have been displaced. Throughout the specification and claims, it should be remembered that the term "PEG" includes structures having various terminal or "end capping" groups and so forth. The term "PEG" also means a polymer that contains a majority, that is to say, greater than 50%, of —$OCH_2CH_2$— repeating subunits. With respect to specific forms, the PEG can take any number of a variety of molecular weights, as well as structures or geometries such as "branched," "linear," "forked," "multifunctional," and the like, to be described in greater detail below.

The terms "end-capped" and "terminally capped" are interchangeably used herein to refer to a terminal or endpoint of a polymer having an end-capping moiety. Typically, although not necessarily, the end-capping moiety comprises a hydroxy or $C_{1-20}$ alkoxy group, more preferably a $C_{1-10}$ alkoxy group, and still more preferably a $C_{1-5}$ alkoxy group. Thus, examples of end-capping moieties include alkoxy (e.g., methoxy, ethoxy and benzyloxy), as well as aryl, heteroaryl, cyclo, heterocyclo, and the like. It must be remembered that the end-capping moiety may include one or more atoms of the terminal monomer in the polymer [e.g., the end-capping moiety "methoxy" in $CH_3O(CH_2CH_2O)_n$— and $CH_3(OCH_2CH_2)_n$—]. In addition, saturated, unsaturated, substituted and unsubstituted forms of each of the foregoing are envisioned. Moreover, the end-capping group can also be a silane. The end-capping group can also advantageously comprise a detectable label. When the polymer has an end-capping group comprising a detectable label, the amount or location of the polymer and/or the moiety (e.g., active agent) to which the polymer is coupled can be determined by using a suitable detector. Such labels include, without limitation, fluorescers, chemiluminescers, moieties used in enzyme labeling, colorimetric (e.g., dyes), metal ions, radioactive moieties, and the like. Suitable detectors include photometers, films, spectrometers, and the like. The end-capping group can also advantageously comprise a phospholipid. When the polymer has an end-capping group comprising a phospholipid, unique properties are imparted to the polymer and the resulting conjugate. Exemplary phospholipids include, without limitation, those selected from the class of phospholipids called phosphatidylcholines. Specific phospholipids include, without limitation, those selected from the group consisting of dilauroylphosphatidylcholine, dioleylphosphatidylcholine, dipalmitoylphosphatidylcholine, disteroylphosphatidylcholine, behenoylphosphatidylcholine, arachidoylphosphatidylcholine, and lecithin.

"Non-naturally occurring" with respect to a polymer as described herein, means a polymer that in its entirety is not found in nature. A non-naturally occurring polymer of the invention may, however, contain one or more monomers or segments of monomers that are naturally occurring, so long as the overall polymer structure is not found in nature.

The term "water soluble" as in a "water-soluble polymer" is any polymer that is soluble in water at room temperature.

Typically, a water-soluble polymer will transmit at least about 75%, more preferably at least about 95%, of light transmitted by the same solution after filtering. On a weight basis, a water-soluble polymer will preferably be at least about 35% (by weight) soluble in water, more preferably at least about 50% (by weight) soluble in water, still more preferably about 70% (by weight) soluble in water, and still more preferably about 85% (by weight) soluble in water. It is most preferred, however, that the water-soluble polymer is about 95% (by weight) soluble in water or completely soluble in water.

Molecular weight in the context of a water-soluble polymer of the invention, such as PEG, can be expressed as either a number average molecular weight or a weight average molecular weight. Unless otherwise indicated, all references to molecular weight herein refer to the weight average molecular weight. Both molecular weight determinations, number average and weight average, can be measured using gel permeation chromatography or other liquid chromatography techniques. Other methods for measuring molecular weight values can also be used, such as the use of end-group analysis or the measurement of colligative properties (e.g., freezing-point depression, boiling-point elevation, or osmotic pressure) to determine number average molecular weight or the use of light scattering techniques, ultracentrifugation or viscometry to determine weight average molecular weight. The polymers of the invention typically possess low polydispersity values, preferably less than about 1.2, more preferably less than about 1.15, still more preferably less than about 1.10, yet still more preferably less than about 1.05, and most preferably less than about 1.03.

The term "active" or "activated" when used in conjunction with a particular functional group, refers to a reactive functional group that reacts readily with an electrophile or a nucleophile on another molecule. This is in contrast to those groups that require strong catalysts or highly impractical reaction conditions in order to react (i.e., a "non-reactive" or "inert" group).

As used herein, the term "functional group" or any synonym thereof is meant to encompass protected forms thereof as well as unprotected forms. The terms "protected," "protecting group" and "protective group" refer to the presence of a moiety (i.e., the protecting group) that prevents or blocks reaction of a particular chemically reactive functional group in a molecule under certain reaction conditions. The protecting group will vary depending upon the type of chemically reactive group being protected as well as the reaction conditions to be employed and the presence of additional reactive or protecting groups in the molecule, if any. Protecting groups known in the art can be found in Greene, T. W., et al., PROTECTIVE GROUPS IN ORGANIC SYNTHESIS, 3rd ed., John Wiley & Sons, Inc., New York, N.Y. (1999).

The terms "spacer moiety," "linkage" or "linker" are used herein to refer to an atom or a collection of atoms optionally used to link interconnecting moieties. The spacer moiety may be hydrolytically stable or may include a physiologically hydrolyzable or enzymatically degradable linkage.

"Alkyl" refers to a hydrocarbon chain, typically ranging from about 1 to 15 atoms in length. Such hydrocarbon chains are preferably but not necessarily saturated and may be branched or straight chain, although typically straight chain is preferred. Exemplary alkyl groups include methyl, ethyl, propyl, butyl, pentyl, 1-methylbutyl, 1-ethylpropyl, 3-methylpentyl, and the like. As used herein, "alkyl" includes "lower alkyl", "cycloalkyl", and "cycloalkylene".

"Lower alkyl" refers to an alkyl group containing from 1 to 6 carbon atoms, and may be straight chain or branched, as exemplified by methyl, ethyl, n-butyl, i-butyl, and t-butyl.

"Cycloalkyl" refers to a saturated or unsaturated cyclic hydrocarbon chain, including bridged, fused, or Spiro cyclic compounds, preferably made up of 3 to about 12 carbon atoms, more preferably 3 to about 8 carbon atoms. "Cycloalkylene" refers to a cycloalkyl group that is inserted into an alkyl chain by bonding of the chain at any two carbons in the cyclic ring system.

"Alkoxy" refers to an —O—R group, wherein R is alkyl or substituted alkyl, preferably $C_{1-6}$ alkyl (e.g., methoxy, ethoxy, propyloxy, and so forth).

The term "substituted" as in, for example, "substituted alkyl," refers to a moiety (e.g., an alkyl group) substituted with one or more noninterfering substituents, such as, but not limited to: alkyl, $C_{3-8}$ cycloalkyl, e.g., cyclopropyl, cyclobutyl, and the like; halo, e.g., fluoro, chloro, bromo, and iodo; cyano; alkoxy, lower phenyl; substituted phenyl; and the like. "Substituted aryl" is aryl having one or more noninterfering groups as a substituent. For substitutions on a phenyl ring, the substituents may be in any orientation (i.e., ortho, meta, or para).

"Noninterfering substituents" are those groups that, when present in a molecule, are typically nonreactive with other functional groups contained within the molecule.

"Aryl" means one or more aromatic rings, each of 5 or 6 core carbon atoms. Aryl includes multiple aryl rings that may be fused, as in naphthyl or unfused, as in biphenyl. Aryl rings may also be fused or unfused with one or more cyclic hydrocarbon, heteroaryl, or heterocyclic rings. As used herein, "aryl" includes "heteroaryl".

"Heteroaryl" is an aryl group containing from one to four heteroatoms, preferably sulfur, oxygen, or nitrogen, or a combination thereof. Heteroaryl rings may also be fused with one or more cyclic hydrocarbon, heterocyclic, aryl, or heteroaryl rings.

"Heterocycle" or "heterocyclic" means one or more rings of 5-12 atoms, preferably 5-7 atoms, with or without unsaturation or aromatic character and having at least one ring atom that is not a carbon. Preferred heteroatoms include sulfur, oxygen, and nitrogen.

"Substituted heteroaryl" is heteroaryl having one or more noninterfering groups as substituents.

"Substituted heterocycle" is a heterocycle having one or more side chains formed from noninterfering substituents.

An "organic radical" as used herein shall include alkyl, substituted alkyl, aryl and substituted aryl.

"Electrophile" and "electrophilic group" refer to an ion or atom or collection of atoms, that may be ionic, having an electrophilic center, i.e., a center that is electron seeking, capable of reacting with a nucleophile.

"Nucleophile" and "nucleophilic group" refers to an ion or atom or collection of atoms that may be ionic having a nucleophilic center, i.e., a center that is seeking an electrophilic center or with an electrophile.

A "hydrolyzable" or "degradable" bond is a bond that reacts with water (i.e., is hydrolyzed) under physiological conditions. The tendency of a bond to hydrolyze in water will depend not only on the general type of linkage connecting two atoms but also on the substituents attached to these atoms. Appropriate hydrolytically unstable or weak linkages include but are not limited to carboxylate ester, phosphate ester, anhydrides, acetals, ketals, acyloxyalkyl ether, imines, orthoesters, peptides and oligonucleotides.

An "enzymatically degradable linkage" means a linkage that is subject to degradation by one or more enzymes.

A "hydrolytically stable" linkage or bond refers to a chemical bond, typically a covalent bond, that is substantially stable in water, that is to say, does not undergo hydrolysis under physiological conditions to any appreciable extent over an extended period of time. Examples of hydrolytically stable linkages include, but are not limited to, the following: carbon-carbon bonds (e.g., in aliphatic chains); ethers, amides, urethanes, and the like. Generally, a hydrolytically stable linkage is one that exhibits a rate of hydrolysis of less than about 1-2% per day under physiological conditions. Hydrolysis rates of representative chemical bonds can be found in most standard chemistry textbooks.

"Pharmaceutically acceptable excipient or carrier" refers to an excipient that may optionally be included in the compositions of the invention and that causes no significant adverse toxicological effects to the patient. "Pharmacologically effective amount," "physiologically effective amount," and "therapeutically effective amount" are used interchangeably herein to mean the amount of a conjugate that is needed to provide a desired level of the conjugate in the bloodstream or in the target tissue. The precise amount will depend upon numerous factors, e.g., the conjugate, the components and physical characteristics of the therapeutic composition, intended patient population, individual patient considerations, and the like, and can readily be determined by one skilled in the art, based upon the information provided herein.

"Multi-functional" means a polymer having three or more functional groups contained therein, where the functional groups may be the same or different. Exemplary ranges for number of functional groups for a multi-functional polymer include: 3-100 functional groups; 3-50 functional groups; 3-25 functional groups; 3-15 functional groups; 3 to 10 functional groups. Typically, the number of functional groups for a multi-functional polymer is one of 3, 4, 5, 6, 7, 8, 9 or 10 functional groups.

The term "patient," refers to a living organism suffering from or prone to a condition that can be prevented or treated by administration of an active agent (e.g., conjugate), and includes both humans and animals.

"Optional" or "optionally" means that the subsequently described circumstance may or may not occur, so that the description includes instances where the circumstance occurs and instances where it does not.

"Substantially" (unless specifically defined for a particular context elsewhere or the context clearly dictates otherwise) means nearly totally or completely, for instance, satisfying one or more of the following: greater than 50%, 51% or greater, 75% or greater, 80% or greater, 90% or greater, and 95% or greater of the condition.

The phrase "ratio of α-epimers and β-epimers is at least" means that α-epimers are present in the stated ratio or in an amount greater than the stated ratio. For example, if the "ratio of α-epimers and β-epimers is at least 60 to 40" then there are 6 α-epimers for every 4 β-epimers or more than 6 α-epimers for every 4 β-epimers (e.g., 70 α-epimers for every 30 β-epimers).

Unless the context clearly dictates otherwise, when the term "about" precedes a numerical value, the numerical value is understood to mean±10% of the stated numerical value.

Turning to one or more embodiments of the invention, a synthetic method is provided, the synthetic method comprising stereoselectively reducing a ketone of a morphinone to form a reduced morphinone. The morphinone is a phenanthrene-based moiety that (a) comprises the following structure:

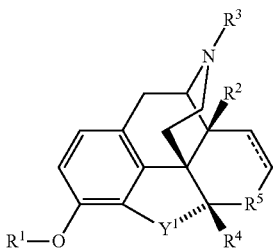

Formula I wherein:
$R^1$ is H, an organic radical, or a hydroxyl protecting group;
$R^2$ is H or OH;
$R^3$ is H or an organic radical, (preferably $R^3$ is H or an organic radical with the proviso that when $R^3$ is an organic radical, the organic radical is not

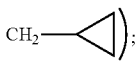;

$R^4$ is H or an organic radical;
the dotted line ("---") represents an optional double bond;
$Y^1$ is O or S; and
$R^5$ is selected from the group consisting of

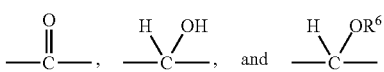

(without regard to stereochemistry), wherein $R^6$ is an organic radical); and (b) contains a ketone [either pursuant to the structure defined for the phenanthrene-based moiety provided in (a), i.e., Formula I, or by replacement of atom in the phenanthrene-based moiety provided in (a), i.e., Formula I, for a ketone].

It is particularly preferred that the morphinone comprises the following structure:

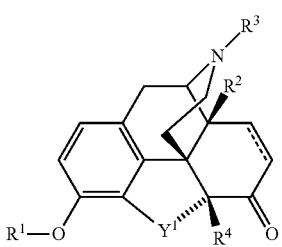

Formula II wherein:
$R^1$ is H, an organic radical or a hydroxyl protecting group;
$R^2$ is H or OH;
$R^3$ is H or an organic radical, with the proviso that when $R^3$ is an organic radical, the organic radical is not

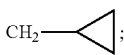;

$R^4$ is H or an organic radical;

the dotted line ("---") represents an optional double bond; and $Y^1$ is O or S.

The step of stereoselectively reducing a ketone of a ketone-containing morphinone typically comprises adding a stereoselective reducing agent (by, for example, adding a composition comprising the stereoselective reducing agent) to a composition comprising the morphinone.

Any reducing agent known to one skilled in the art can serve as a selective reducing agent so long as the reducing agent is stereoselective. In the present context, a reducing agent is considered stereoselective when the composition following the reducing step comprises a reduced morphinone of a specific epimer that is in an amount at least 65% on a molar basis relative to the starting molar amount of the corresponding "non-reduced" morphinone. Exemplary values representing the amount (on a molar basis relative to the starting molar amount of the corresponding "non-reduced" morphinone) of the reduced morphinone produced using the selective reducing agent include: at least at least 70%; at least 75%; at least 80%; at least 85%; at least 90%; at least 92%; at least 94%; at least 95%; at least 96%; at least 97%; at least 98%; at least 99%; at least 99.5%, and at least 99.9%.

Experimentation using techniques known to those of ordinary skill in the art can be used to determine whether a given reducing agent is a stereoselective reducing agent (i.e., a reducing agent that will provide a composition comprising a reduced morphinone of a specific epimer in an amount of at least 65% on a molar basis relative to the starting molar amount of the corresponding "non-reduced" morphinone). For example, a composition comprising a proposed reducing agent can be combined with a composition containing the morphinone. An aliquot of the resulting composition can be separated by epimer and the amount of each epimer calculated using conventional techniques (such as, for example, using high performance liquid chromatography with a chiral column, mass spectrometry, electrochromatography, capillary electrophoresis, and nuclear magnetic resonance). If the reducing agent used results in an acceptable amount of a single epimer (e.g., at least 65% on a molar basis relative to the starting molar amount of the corresponding "non-reduced" morphinone), then the proposed reducing agent is a stereoselective reducing agent suited for carrying out the reducing step.

Examples of stereoselective reducing agents include:

$MB(R^7)_p H_{(4-p)}$, wherein M is selected from the group consisting of lithium ("Li"), sodium ("Na") and potassium ("K"), $R^7$ (in each occurrence) is independently selected from the group consisting of straight alkyl having 1-10 carbon atoms, branched alkyl having 1-10 carbon atoms, substituted aryl, unsubstituted aryl, straight alkoxy having 1-10 carbon atoms, branched alkoxy having 1-10 carbon atoms, and $R^8C(O)$—O— wherein $R^8$ is an organic radical (typically having 1-10 carbon atoms), and (p) is an integer selected from the group consisting of 1, 2 and 3;

$M_q Al(R^7)_p H_{[(3+s)-p]}$, wherein M is selected from the group consisting of lithium ("Li"), sodium ("Na") and potassium ("K"), $R^7$ (in each occurrence) is independently selected from the group consisting of straight and branched alkyl having 2-7 carbon atoms, (q) is zero or one, and (p) is an integer selected from the group consisting of 1, 2 and 3;

$MAl(OR^8)_p H_{(4-p)}$, wherein M is selected from the group consisting of lithium ("Li"), sodium ("Na") and potassium ("K"), $R^8$ (in each occurrence) is independently selected from the group consisting of straight and branched alkyl having 2-7 carbon atoms and $R^9$—O—$R^{10}$— (wherein $R^8$, in each occurrence, is independently straight or branched alkyl of 1-3 carbon atoms and $R^9$ and $R^{10}$ is independently 1,2-$C_{2-3}$alkylnene or 1,3 propylene), and (p) is an integer selected from the group consisting of 1, 2 and 3;

and combinations thereof

In addition, the selective reducing agent can be selected from the group consisting of lithium triethylborohydride, sodium triethylborohydride, potassium triethylborohydride, sodium triacetoxyborohydride, potassium triacetoxyborohydride, lithium tri-sec-butylborohydride, sodium tri-sec-butylborohydride, potassium tri-sec-butylborohydride, lithium 9-borabicyclo[3.3.1]-nonane (9-BBN) hydride, lithium hexylborohydride, lithium trisiamylborohydride, potassium trisiamylborohydride, lithium triethylborodeuteride, LiAlH $(CEt_2CMe_3)_3$, and combinations thereof.

The step of stereoselectively reducing a ketone of a morphinone is typically conducted under conditions (e.g., solvent, temperature, amount, and so forth) either known to those of ordinary skill in the art or that can be determined without undue experimentation. Exemplary conditions will now be provided.

Addition of the stereoselective reducing agent to a composition comprising the morphinone is typically carried out in the presence of an organic solvent that is not readily reactive with reducing agents. Exemplary organic solvents that are not readily reactive with reducing agents include organic solvents selected from the group consisting of aliphatic hydrocarbons, aromatic hydrocarbons, ethers, cyclic ethers, and combinations thereof. Additional exemplary solvents include those solvents selected from the group consisting of toluene, methyl t-butyl, tetrahydrofuran, hexane, cyclohexane, ethyl ether, diethyl ether, benzene and combinations thereof. Preferred organic solvents include those selected from the group consisting of diethyl ether and tetrahydrofuran. One of ordinary skill in the art can determine whether any particular solvent can serve as a solvent for carrying out the reduction step by, for example, carrying out the method using the proposed solvent and then testing for the presence of the reduced morphinone. If the solvent used results in an acceptable amount (e.g., at least 65% on a molar basis relative to the starting molar amount of the corresponding "non-reduced" morphinone), then the proposed solvent is a solvent suited for carrying out the reducing step.

Addition of the stereoselective reducing agent to a composition comprising the morphinone is typically carried out at a temperature of from about −100° C. to about 90° C. Exemplary ranges of temperature at which the addition of the stereoselective reducing agent is carried out include the following: from about −90° C. to about 80° C.; from about −80° C. to about 70° C.; from about −70° C. to about 50° C.; from about −60° C. to about 30° C.; from about −50° C. to about 20° C.; from about −40° C. to about 10° C.; from about −30° C. to about 0° C.; from about −20° C. to about 20° C.; from about −20° C. to about 10° C.; and from about −20° C. to 0° C. One of ordinary skill in the art can determine whether any particular temperature can serve as a temperature for carrying out the reduction step by, for example, carrying out the method using the proposed temperature and then testing for the presence of the reduced morphinone. If the temperature used results in an acceptable amount (e.g., at least 65% on a molar basis relative to the starting molar amount of the corresponding "non-reduced" morphinone), then the proposed temperature is a temperature suited for carrying out the reducing step.

Addition of the stereoselective reducing agent to a composition comprising the morphinone is typically carried out such that the stereoselective reducing agent is added in excess. Exemplary molar ratios for carrying out the reducing step include the following (stereoselective reducing agent to morphinone): 50:1; 20:1; 15:1; 10:1; 9:1; 8:1; 7:1; 6:1; 5:1; 4:1; 3:1; 2:1; 1.8:1; 1.6:1; 1.4:1; 1.2:1; 1:1; 1:1.2; 1:1.4; 1:1.6; 1:1.8; 1:2; 1:3; 1:4; 1:5; 1:6; 1:7; 1:8; 1:9; 1:10; 1:15; 1:20; and 1:50, with the following ratios being preferred: 2:1; 1.8:1; 1.6:1; 1.4:1; 1.2:1; 1:1; 1:1.2; 1:1.4; 1:1.6; 1:1.8; and 1:2. One of ordinary skill in the art can determine whether any ratio can serve as a ratio for carrying out the reducing step by, for example, carrying out the reducing step using the proposed ratio and then testing for the presence of reduced morphinone. If the ratio used results in an acceptable amount (e.g., at least 65% on a molar basis relative to the starting molar amount of the corresponding "non-reduced" morphinone), then the proposed ratio is a ratio suited for carrying out the reducing step.

Once the stereoselective reducing agent has been added to the composition comprising the morphinone (to thereby allow for stereoselective reduction), stereoselective reduction is allowed to proceed for a period of time so as to result in the reduced morphinone. A specific period of time sufficient to result in the reduced morphinone will vary depending on the solvent, temperature, molar amounts of reactants, and so forth. Typically, however, the amount of time the stereoselective reduction will take place will satisfy at one or more of the following ranges: not longer than about 5 minutes, not longer than about 10 minutes, not longer than about 30 minutes, not longer than about 1 hour; not longer than about 1.5 hours, not longer than about 2 hours, not longer than about 2.5 hours; not longer than about 3 hours; not longer than about 4 hours; not longer than about 5 hours; not longer than about 8 hours; not longer than about 10 hours; not longer than about 12 hours; not longer than about 16 hours; not longer than about 20 hours; not longer than about 24 hours; not longer than about 36 hours; and not longer than about 48 hours. In this regard, a preferred time period is about 10 minutes to about 2 hours.

The "morphinone" as used herein, refers to a phenanthrene-based moiety that (a) comprises the following structure:

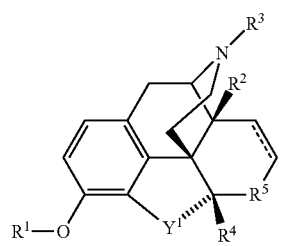

Formula I wherein:
  $R^1$ is H, an organic radical, or a hydroxyl protecting group;
  $R^2$ is H or OH;
  $R^3$ is H or an organic radical, with the proviso that when $R^3$ is an organic radical, the organic radical is not

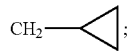;

$R^4$ is H or an organic radical;
  the dotted line ("---") represents an optional double bond;
  $Y^1$ is O or S; and
  $R^5$ is selected from the group consisting of

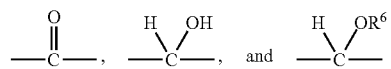

(wherein $R^6$ is an organic radical); and (b) contains a ketone [either pursuant to the structure defined for the phenanthrene-based moiety provided in (a), i.e., Formula I, or by replacement of atom in the phenanthrene-based moiety provided in (a), i.e., Formula I, for a ketone]. The morphinone may comprise more than a single ketone. When the morphinine comprises more than a single ketone, the use of a chemoselective and stereoselective reagent is necessary in order to carry out the present invention. Approaches for chemoselective reduction are known to those of ordinary skill in the art [see, for example, Larock (1989) *Comprehensive Organic Transformations* VCH: NY, p. 993] and/or can be determined without undue experimentation. Preferably, the morphinone is a phenanthrene-based moiety (as defined with regard to Formula I) wherein $R^5$ is

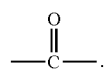.

A preferred morphinone comprises the following structure:

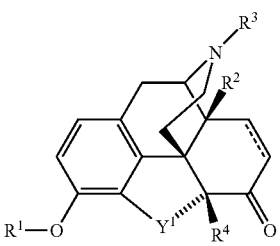

Formula II wherein:
  $R^1$ is H, an organic radical or a hydroxyl protecting group;
  $R^2$ is H or OH (preferably OH);
  $R^3$ is H or an organic radical, with the proviso that when $R^3$ is an organic radical, the organic radical is not

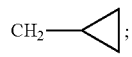;

$R^4$ is H or an organic radical (preferably H);
  the dotted line ("---") represents an optional double bond; and
  $Y^1$ is O or S (preferably O).

With respect to morphinones that include a hydroxyl protecting group (e.g., when $R^1$ is a hydroxyl protecting group in Formula I and Formula II), the hydroxyl protecting group can be any group capable of protecting a free hydroxyl group which, subsequent to the reaction for which protection is employed, may be removed without disturbing the remainder of the molecule. A variety of protecting groups for the hydroxyl group, synthesis thereof, and methods for adding and removing the protective group(s) can be found in Greene, T., and Wuts, Peter G. M., "PROTECTIVE GROUPS IN ORGANIC SYNTHESIS," Chapter 6, 3$^{rd}$ Edition, John Wiley and Sons, Inc., New York, 1999. Specific and nonlimiting examples of hydroxyl protecting groups (e.g., $R^1$ in Formula I and Formula II) include alkanoyl having 2 to 5 carbons (such as acetyl), aryloyl having 7 to 11 carbons (such as benzoyl), benzyl, 1-ethoxyethyl, methoxymethyl, 4-methoxyphenylmethyl methoxymethyl, methoxyethoxymethylene, 1-ethoxyethyl, benzyloxymethyl, (β-trimethylsilylethoxy)methyl, tetrahydropyranyl, 2,2,2-trichloroethoxycarbonyl, t-butyl (diphenyl)silyl, trialkylsilyl, trichloromethoxycarbonyl, and 2,2,2-trichloroethoxymethyl.

A protected hydroxyl group of the reduced morphinone can be deprotected (i.e., the original hydroxyl group "regenerated") using conventional techniques. Such techniques are known to those of ordinary skill in the art and are described in Greene et al., infra. Optionally, the methods described herein include carrying out a deprotecting step to remove the hydroxyl protecting group (when present) following attachment of a water-soluble polymer.

Exemplary morphinones useful in the present invention include:

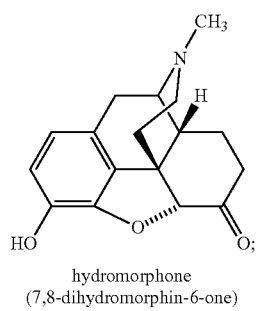

hydromorphone
(7,8-dihydromorphin-6-one)

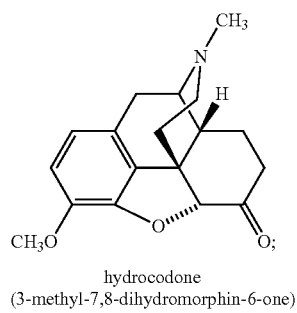

hydrocodone
(3-methyl-7,8-dihydromorphin-6-one)

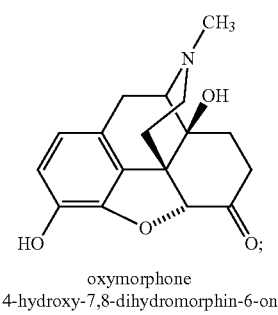

oxymorphone
(14-hydroxy-7,8-dihydromorphin-6-one)

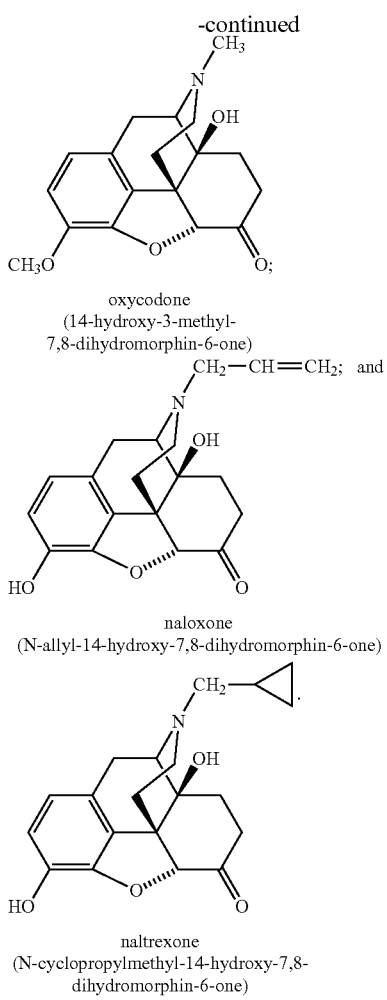

oxycodone
(14-hydroxy-3-methyl-
7,8-dihydromorphin-6-one)

naloxone
(N-allyl-14-hydroxy-7,8-dihydromorphin-6-one)

naltrexone
(N-cyclopropylmethyl-14-hydroxy-7,8-
dihydromorphin-6-one)

These and other morphinones have been described and characterized previously. See, for example: U.S. Pat. Nos. 2,628,962, 2,654,756 and 2,649,454 (hydromorphone and others); U.S. Pat. No. 2,715,626 (hydrocodone and others); U.S. Pat. No. 2,806,033 (oxymorphone and others); Freund et al. (1916) J. Prak. Chemie 94:135-178 (oxycodone); U.S. Pat. No. 3,254,088 (naloxone and others); and U.S. Pat. No. 3,332,950 (naltrexone and others).

Optionally, the method further comprises the step of covalently attaching a water-soluble polymer to the reduced morphinone. Any approach for covalently attaching the water-soluble polymer to the reduced morphinone can be used and the invention is not limited in this regard. Advantageously, a hydroxyl group of the reduced morphinone can serve as an attachment point for the water-soluble polymer. Typically, the hydroxyl group serving as the point of attachment for the water-soluble polymer will be the hydroxyl group generated following stereoselective reduction a ketone of a morphinone.

For example, as described in U.S. Patent Application Publication 2005/0136031, a reduced morphinone bearing a hydroxyl group can be placed under basic conditions to thereby form the corresponding alkoxide group. Thereafter, a halo-substituted, water-soluble polymer can be added to the reduced morphinone to form an ether-linked conjugate. A method for preparing a halo-substituted, water-soluble polymer is described in U.S. Patent Application Publication 2005/0136031.

In addition, a reduced morphinone bearing a hydroxyl group can be reacted in a suitable organic solvent with a water-soluble polymer bearing a leaving group, such as a sulfonate-based leaving group (e.g., a mesylate, tresylate and tosylate leaving groups).

In addition, a carboxylic acid-terminated, water-soluble polymer can be added to the reduced morphine to form the conjugate via an esterification reaction. Such an esterification reaction is conducted in the presence of an acid (e.g., $H_2SO_4$), typically with removing water by azeotropic distillation, addition of a dehydrating agent, or use of a molecular sieve. Methods for preparing carboxylic acid-terminated, water-soluble polymers are described in U.S. Pat. No. 5,672,662.

In certain instances, however, the morphinone may include more than a single hydroxyl group (e.g., when $R^1$ is H and $R^2$ is OH in Formula II), which may result in difficulty in directing conjugation at the desired hydroxyl group. In such an instance, it may be desired to protect the hydroxyl group(s) of a hydroxyl-containing morphinone with hydroxyl protecting group(s) prior to carrying out the conjugation step. In this way, the hydroxyl group(s) is/are "protected" from the conjugation at one or more undesired locations. In some instances, it will be advantageous to carryout the protecting step prior to stereoselective reduction of the ketone of the morphinone so that hydroxyl group protection does not compete for the hydroxyl group resulting from stereoselective reduction of the ketone group of the morphinone.

In other instances, it is not necessary to protect one or more of the hydroxyl groups of a morphinone. Examples where it is not necessary to protect the hydroxyl group include the instances when hydroxyl group conjugation would not result in a deleterious product and/or when the hydroxyl group is not readily conjugated, for example, steric effects. Determining whether any given hydroxyl group should be protected can be performed by one of ordinary skill in the art. For example, a first composition containing a proposed morphinone having a hydroxyl group in protected form and a second composition containing the corresponding morphine having the hydroxyl group in unprotected form can be exposed to conjugation conditions. Upon removal of the protected hydroxyl group from the morphinone in the first composition, it is possible to test the structure of the conjugates from each of the two compositions using, for example, chromatography and/or nuclear magnetic resonance techniques. If the structures are substantially the same (e.g., both compositions are substantially identical with respect to the number and attachment location of the water-soluble polymer), then it is not necessary to protect the particular hydroxyl group prior to carrying out conjugation with that particular morphinone.

The Water-soluble Polymer (Prior to the Optional Step of Covalently Attaching a Water-Soluble Polymer to the Reduced Morphinone)

With respect to the water-soluble polymer, the water-soluble polymer is nonpeptidic, nontoxic, non-naturally occurring and biocompatible. With respect to biocompatibility, a substance is considered biocompatible if the beneficial effects associated with use of the substance alone or with another substance in connection with living tissues (e.g., administration to a patient) outweighs any deleterious effects as evaluated by a clinician, e.g., a physician. With respect to non-immunogenicity, a substance is considered nonimmunogenic if the intended use of the substance in vivo does not produce an undesired immune response (e.g., the formation of antibodies) or, if an immune response is produced, that such a response is not deemed clinically significant or important as evaluated by a clinician. It is particularly preferred that the nonpeptidic water-soluble polymer is biocompatible and nonimmunogenic.

Examples of water-soluble polymers include, but are not limited to, poly(alkylene glycols) such as polyethylene glycol (PEG), polypropylene glycol) ("PPG"), copolymers of ethylene glycol and propylene glycol and the like, poly(oxyethylated polyol), poly(olefinic alcohol), poly(vinylpyrrolidone), poly(hydroxyalkylmethacrylamide), poly(hydroxyalkylmethacrylate), poly(saccharides), poly($\alpha$-hydroxy acid), poly(vinyl alcohol), polyphosphazene, polyoxazoline, poly(N-acryloylmorpholine), and combinations of any of the foregoing.

The polymer is not limited to a particular structure and can be linear (e.g., alkoxy PEG or bifunctional PEG), branched or multi-armed (e.g., forked PEG or PEG attached to a polyol core), dendritic, or with degradable linkages. Moreover, the internal structure of the polymer can be organized in any number of different patterns and can be selected from the group consisting of homopolymer, alternating copolymer, random copolymer, block copolymer, alternating tripolymer, random tripolymer, and block tripolymer.

Typically, the water-soluble polymer used in the optional step of covalently attaching a water-soluble polymer to the reduced morphinone is an activated water-soluble polymer (such as an activated PEG) typically referred to as a "polymeric reagent." Thus, a polymeric reagent will possess a reactive group for reaction with the reduced morphinone Representative polymeric reagents and methods for conjugating these polymers to an active moiety are known in the art and further described in the literature. See, for example, U.S. Patent Application Publication Nos. 2003/0124086 and 2005/0136031.

Typically, the weight-average molecular weight of the water-soluble polymer in the conjugate is from about 100 Daltons to about 5,000 Daltons. Exemplary ranges, however, include weight-average molecular weights in the range of greater than 100 Daltons to less than 5,000 Daltons, in the range of from about 100 Daltons to about 4,750 Daltons, in the range of from about 100 Daltons to about 4,500 Daltons, in the range of greater than 100 Daltons to about 4,500 Daltons, in the range of from about 100 Daltons to about 4,250 Daltons, in the range of from about 100 Daltons to about 3,750 Daltons, in the range of from about 100 Daltons to about 3,500 Daltons, in the range of from about 100 Daltons to about 3,250 Daltons, in the range of from about 100 Daltons to about 3,000 Daltons, in the range of from about 100 Daltons to about 2,750 Daltons, in the range of from about 100 Daltons to about 2,500 Daltons, in the range of from about 100 Daltons to about 2,250 Daltons, in the range of from about 100 Daltons to about 2,000 Daltons, in the range of from about 100 Daltons to about 1,750 Daltons, in the range of from about 100 Daltons to about 1,500 Daltons, in the range of from about 100 Daltons to about 1,500 Daltons, in the range of from about 100 Daltons to about 1,250 Daltons, in the range of from about 100 Daltons to about 1,000 Daltons, in the range of from about 100 Daltons to about 900 Daltons, in the range of from about 100 Daltons to about 800 Daltons, in the range of from about 100 Daltons to about 700 Daltons, in the range of from about 100 Daltons to about 600 Daltons, in the range of from about 100 Daltons to about 500 Daltons, in the range of from about 100 Daltons to about 400 Daltons, in the range of from about 100 Daltons to about 300 Daltons, in the range of from about 200 Daltons to about 2,000 Daltons, in the range of from about 300 Daltons to about 1000 Daltons, in the range of from about 300 Daltons to about 1,500 Daltons, and in the range of from about 50 Daltons to about 1,500 Daltons. For any given water-soluble polymer, PEGs having a molecular weight in one or more of these ranges are preferred.

Exemplary weight-average molecular weights for the water-soluble polymer include about 100 Daltons, about 200 Daltons, about 300 Daltons, about 400 Daltons, about 500 Daltons, about 600 Daltons, about 700 Daltons, about 750 Daltons, about 800 Daltons, about 900 Daltons, about 1,000 Daltons, about 1,250, about 1,500 Daltons, about 1,750 Daltons, about 2,000 Daltons, about 2,250 Daltons, about 2,500 Daltons, about 2,750 Daltons, about 3,000 Daltons, about 3,250 Daltons, about 3,500 Daltons, about 3,750 Daltons, about 4,000 Daltons, about 4,250 Daltons, about 4,500 Daltons, about 4,750 Daltons, and about 5,000 Daltons. Branched versions of the water-soluble polymer (e.g., a branched 5,000 Dalton water-soluble polymer comprised of two 2,500 Dalton polymers) having a total molecular weight of any of the foregoing can also be used.

When used as the polymer, PEGs will typically comprise a number of ($OCH_2CH_2$) monomers [or ($CH_2CH_2O$) monomers, depending on how the PEG is defined]. As used throughout the description, the number of repeating units is identified by the subscript "n" in "($OCH_2CH_2$)$_n$," or "($CH_2CH_2O$)$_n$." Thus, the value of (n) typically falls within one or more of the following ranges: from 2 to about 113, from about 2 to about 102, from about 2 to about 91, from about 2 to about 80, from about 2 to about 68, from about 2 to about 57, from about 2 to about 45, from about 2 to about 34, from about 2 to about 23, from about 2 to about 20, and from about 2 to about 15. Example values of (n) include: 2, 3, 4, 5, 6, 7, 8, 9, 10, 11, 12, 13, 14, 15, 16, 17, 18, 19, and 20. For any given polymer in which the molecular weight is known, it is possible to determine the number of repeating units (i.e., "n") by dividing the total weight-average molecular weight of the polymer by the molecular weight of the repeating monomer.

One particularly preferred polymer for use in the invention is an end-capped polymer, that is, a polymer having at least one terminus capped with a relatively inert group, such as a lower $C_{1-6}$ alkoxy group, although a hydroxyl group can also be used. When the polymer is PEG, for example, it is preferred to use a methoxy-PEG (commonly referred to as mPEG), which is a linear form of PEG wherein one terminus of the polymer is a methoxy ($-OCH_3$) group, while the other terminus is a hydroxyl or other functional group that can be optionally chemically modified.

In one form useful in one or more embodiments of the present invention, free or unbound PEG is a linear polymer terminated at each end with hydroxyl groups:

$$HO-CH_2CH_2O-(CH_2CH_2O)_n-CH_2CH_2-OH,$$

wherein (n) ranges from zero to about 4,000.

The above polymer, alpha-, omega-dihydroxylpoly(ethylene glycol), can be represented in brief form as HO-PEG-OH where it is understood that the -PEG-symbol can represent the following structural unit:

$$-CH_2CH_2O-(CH_2CH_2O)_n-CH_2CH_2-,$$

wherein (n) is as defined as above.

Another type of PEG useful in one or more embodiments of the present invention is methoxy-PEG-OH, or mPEG in brief, in which one terminus is the relatively inert methoxy group, while the other terminus is a hydroxyl group. The structure of mPEG is given below.

$$CH_3O-CH_2CH_2O-(CH_2CH_2O)_n-CH_2CH_2-OH$$

wherein (n) is as described above.

Multi-armed or branched PEG molecules, such as those described in U.S. Pat. No. 5,932,462, can also be used as the PEG polymer. For example, PEG can have the structure:

$$\text{poly}_a - P$$
$$R'' - C -$$
$$\text{poly}_b - Q$$

wherein:

$\text{poly}_a$ and $\text{poly}_b$ are PEG backbones (either the same or different), such as methoxy poly(ethylene glycol);

R" is a nonreactive moiety, such as H, methyl or a PEG backbone; and

P and Q are nonreactive linkages. In a preferred embodiment, the branched PEG polymer is methoxy poly(ethylene glycol) disubstituted lysine.

The PEG polymer may comprise a pendant PEG molecule having reactive groups, such as carboxyl, covalently attached along the length of the PEG rather than at the end of the PEG chain. The pendant reactive groups can be attached to the PEG directly or through a spacer moiety, such as an alkylene group.

An exemplary conjugate comprises the following structure:

Formula III $R^1-O$ ... $Y^1$ $R^4$ $(X^1)_a-CH_2CH_2-(OCH_2CH_2)_n-OCH_3$ wherein:

$R^1$ is H or an organic radical (preferably H, hydroxyl protecting group, or lower alkyl such as $CH_3$);

$R^2$ is H or OH (preferably OH);

$R^3$ is H or an organic radical, (preferably, with the proviso that when $R^3$ is an organic radical, the organic radical is not $CH_2-\triangleleft$ ;

$R^4$ is H or an organic radical (preferably H);

the dotted line ("---") represents an optional double bond;

$Y^1$ is O or S;

(n) is an integer (e.g., from 1 to 14);

(a) is either zero or one; and $X^1$, when present, is a spacer moiety (e.g., $-O-$ and $-O-C(O)-$).

The spacer moiety, ("$X^1$") when present, represents the covalent linkage between the water-soluble polymer the reduced morphinone. Exemplary spacer moieties include ether, ester, amide, urethane (also known as carbamate), amine, thioether (also known as sulfide), or urea (also known as carbamide). Nonlimiting examples of specific spacer moieties include those selected from the group consisting of $-O-$, $-S-$, $-S-S-$, $-C(O)-$, $-O-C(O)-$, $-C(O)-O-$, $-C(O)-NH-$, $-NH-C(O)-NH-$, —O—C(O)—NH—, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—CH$_2$—C(O)—NH—, —C(O)—O—CH$_2$—, —CH$_2$—C(O)—O—CH$_2$—, —CH$_2$—CH$_2$—C(O)—O—CH$_2$—, —C(O)—O—CH$_2$—CH$_2$—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$—, —CH$_2$—CH$_2$—NH—C(O)—CH$_2$—CH$_2$—, —C(O)—NH—CH$_2$—, —C(O)—NH—CH$_2$—CH$_2$—, —O—C(O)—NH—CH$_2$—, —O—C(O)—NH—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$—, and —CH$_2$—CH$_2$—CH$_2$—C(O)—NH—CH$_2$—CH$_2$—NH—C(O)—CH$_2$—CH$_2$—.

Optionally, the conjugate of the water-soluble polymer and the reduced morphinone comprises a pharmaceutically acceptable excipient. If desired, the pharmaceutically acceptable excipient can be added to a conjugate to form a composition.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The composition can also include an antimicrobial agent for preventing or deterring microbial growth. Nonlimiting examples of antimicrobial agents suitable for one or more embodiments of the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the composition as well. Antioxidants are used to prevent oxidation, thereby preventing the deterioration of the conjugate or other components of the preparation. Suitable antioxidants for use in one or more embodiments of the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant can be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Acids or bases can be present as an excipient in the composition. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the conjugate in the composition will vary depending on a number of actors, but will optimally be a therapeutically effective dose when the composition is stored in a unit dosage form. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5% to about 98% by weight, more preferably from about 15 to about 95% by weight of the excipient, with concentrations less than 30% by weight most preferred.

These foregoing pharmaceutical excipients along with other excipients are described in "Remington: The Science & Practice of Pharmacy", 19th ed., Williams & Williams, (1995), the "Physician's Desk Reference", 52nd ed., Medical Economics, Montvale, N.J. (1998), and Kibbe, A. H., Handbook of Pharmaceutical Excipients, 3rd Edition, American Pharmaceutical Association, Washington, D.C., 2000.

The compositions comprising the conjugate and any excipient(s) can be further formulated into dosage forms utilizing skills known in the art.

For example, compositions suitable for oral administration can be presented as discrete units such as capsules, cachets, tablets, lozenges, and the like, each containing a predetermined amount of the conjugate as a powder or granules; or a suspension in an aqueous liquor or non-aqueous liquid such as a syrup, an elixir, an emulsion, a draught, and the like.

A tablet may be made by compression or molding, optionally with one or more accessory ingredients. Compressed tablets may be prepared by compressing in a suitable machine, with the conjugate being in a free-flowing form such as a powder or granules which is optionally mixed with a binder, disintegrant, lubricant, inert diluent, surface active agent or dispersing agent. Molded tablets comprised with a suitable carrier may be made by molding in a suitable machine.

A syrup may be made by adding the conjugate to a concentrated aqueous solution of a sugar, for example sucrose, to which may also be added any accessory ingredient(s). Such accessory ingredients may include flavorings, suitable preservatives, an agent to retard crystallization of the sugar, and an agent to increase the solubility of any other ingredient, such as polyhydric alcohol, for example, glycerol or sorbitol.

Formulations suitable for parenteral administration conveniently comprise a sterile aqueous preparation of the conjugate, which can be formulated to be isotonic with the blood of the recipient.

Nasal spray formulations comprise purified aqueous solutions of the conjugate with preservative agents and isotonic agents. Such formulations are preferably adjusted to a pH and isotonic state compatible with the nasal mucous membranes.

Formulations for rectal administration may be presented as a suppository with a suitable carrier such as cocoa butter, or hydrogenated fats or hydrogenated fatty carboxylic acids.

Ophthalmic formulations are prepared by a similar method to the nasal spray, except that the pH and isotonic factors are preferably adjusted to match that of the eye.

Topical formulations comprise the conjugate dissolved or suspended in one or more media such as mineral oil, petroleum, polyhydroxy alcohols or other bases used for topical formulations. The addition of other accessory ingredients as noted above may be desirable.

Pharmaceutical formulations are also provided which are suitable for administration as an aerosol for inhalation. These formulations comprise a solution or suspension of the desired conjugate or a salt thereof. The desired formulation may be placed in a small chamber and nebulized. Nebulization may be accomplished by compressed air or by ultrasonic energy to form a plurality of liquid droplets or solid particles comprising the conjugates or salts thereof.

To the extent the conjugate-containing composition is in liquid or semi-solid form, the liquid or semi-solid can be filled into soft gelatin capsules using appropriate filling machines. Alternatively, such a conjugate-containing composition can also be sprayed, granulated or coated onto a substrate to become a powder, granule or bead that can be further encapsulated or tableted if the compositions solidify at room temperature with or without the addition of appropriate solidifying or binding agents. This approach allows for the creation of a "fused mixture," a "solid solution" or a "eutectic mixture."

The invention also provides a method for administering a conjugate as provided herein to a patient suffering from a condition that is responsive to treatment with conjugate. The method comprises administering to a patient, generally via oral administration, a therapeutically effective amount of the conjugate (preferably provided as part of a pharmaceutical composition).

The method of administering may be used to treat any condition that can be remedied or prevented by administration of the conjugate. Those of ordinary skill in the art appreciate which conditions a specific conjugate can effectively treat. For example, the conjugates can be used to treat patients suffering opioid-induced constipation. Advantageously, the conjugate can be administered to the patient prior to, simultaneously with, or after administration of another active agent.

The actual dose to be administered will vary depending upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a therapeutically effective amount will range from about 0.001 mg to 100 mg, preferably in doses from 0.01 mg/day to 75 mg/day, and more preferably in doses from 0.10 mg/day to 50 mg/day.

The unit dosage of any given conjugate (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration once daily, three times weekly, twice weekly, once weekly, twice monthly, once monthly, and any combination thereof. Once the clinical endpoint has been achieved, dosing of the composition is halted.

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains.

All articles, books, patents and other publications referenced herein are hereby incorporated by reference in their entireties.

EXPERIMENTAL

The practice of the invention will employ, unless otherwise indicated, conventional techniques of organic synthesis, biochemistry, protein purification and the like, which are within the skill of the art. Such techniques are fully explained in the literature. See, for example, J. March, Advanced Organic Chemistry: Reactions Mechanisms and Structure, 4th Ed. (New York: Wiley-Interscience, 1992), supra.

In the following examples, efforts have been made to ensure accuracy with respect to numbers used (e.g., amounts, temperatures, etc.) but some experimental error and deviation should be accounted for. Unless indicated otherwise, temperature is in degrees C. and pressure is at or near atmospheric pressure at sea level. Each of the following examples is considered to be instructive to one of ordinary skill in the art for carrying out one or more of the embodiments described herein.

In the experimental, the following materials (along with their source) were used: sodium borohydride (Aldrich Chemical, Milwaukee Wis.); borane 1.0 M in THF solution (Aldrich Chemical, Milwaukee Wis.); borane diethylaniline (Aldrich Chemical, Milwaukee Wis.); sodium triethylborohydride 1.0 M in THF solution (Aldrich Chemical, Milwaukee Wis.); sodium tri-sec-butylborohydride 1.0 M in THF solution (Aldrich Chemical, Milwaukee Wis., sold under the SELECTRIDE® brand); potassium tri-sec-butylborohydride 1.0 M in THF solution (Aldrich Chemical, Milwaukee Wis., sold under the SELECTRIDE® brand); sodium triacetoxyborohydride (Aldrich Chemical, Milwaukee Wis.); (S)-2-methyl-oxazaborolidine,(S)-MeCBS 1.0 M in toluene (Aldrich Chemical, Milwaukee Wis.) tetrahydrofuran (THF), anhydrous (Aldrich Chemical, Milwaukee Wis.); methanol, anhydrous (Aldrich Chemical, Milwaukee Wis.); ethanol, anhydrous (Aldrich Chemical, Milwaukee Wis.); acetonitrile, anhydrous (Aldrich Chemical, Milwaukee Wis.); dichloromethane (Aldrich Chemical, Milwaukee Wis.); and 3-MEM-O-naloxone was obtained as described in U.S. Patent Application Publication No. 2005/0136031. All $^1$H NMR measurements were performed on a Bruker 300 NMR (Bruker BioSpin, Billerica Mass.).

Example 1

Preparation of Substantially Pure
α-6-OH-3-MEM-O-Naloxol Using
K-tri-sec-butylborohydride

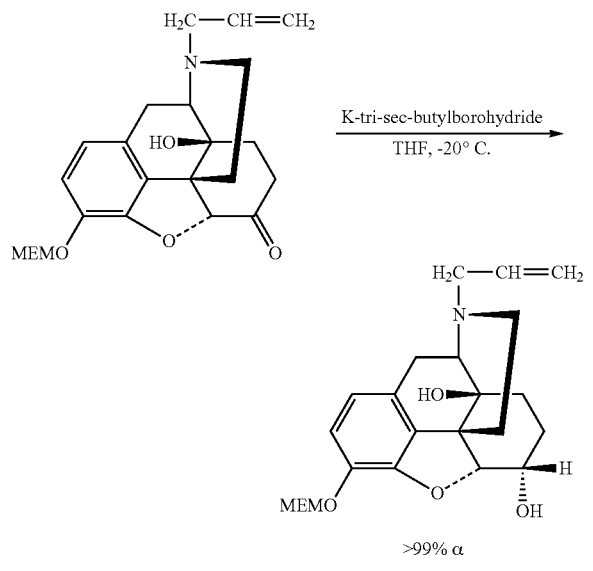

>99% α

To a solution of 3-MEM-O-naloxone base (2.0 g, 4.8 mmol, preparation described in U.S. Patent Application Publication No. 2005/0136031) in dry tetrahydrofuran (50 mL) under an inert atmosphere at −20° C., was added a 1M solution of potassium tri-sec-butylborohydride (7.2 mL, 7.2 mmol) slowly over 15 minutes. The solution was stirred continuously at −20° C. under a nitrogen atmosphere for an additional 1.5 hours and then water (10 mL) was added slowly. The reaction mixture was stirred another 10 minutes at −20° C. and allowed to warm to room temperature. The solvent was removed under reduced pressure and the remaining residue was dissolved in $CH_2Cl_2$ (100 mL). The $CH_2Cl_2$ phase was extracted with a 0.1 N Ha/NaCl water solution (3×100 mL) and the combined aqueous extracts were washed with $CH_2Cl_2$ (1×300 mL). Sodium carbonate was added to bring the aqueous solution to pH=8. The solution was extracted once again with $CH_2Cl_2$ (3×300 mL) and the organic extracts were combined, dried over anhydrous $Na_2SO_4$, filtered, the solvent removed under reduced pressure, and the resulting residue dried overnight in vacuo. The desired product was greater than 99% α-6-OH-3-MEM-O-naloxol. The desired product was obtained as a colorless to slightly yellow viscous liquid (1.7 g, 4.1 mmol, 85% isolated yield). $^1$H NMR ($CDCl_3$, ppm, FIG. 1): δ 6.84 (1H, doublet, aromatic proton of naloxone), 6.59 (1H, doublet, aromatic proton of naloxone), 5.80 (1H, multiplet, olefinic proton of naloxone), 5.56 (1H, doublet, proton of MEM), 5.17 (2H, multiplet, olefinic protons of naloxone), 5.13 (1H, doublet, proton of MEM), 4.61 (1H, doublet, J=4.9 Hz, $C_5$ proton of naloxone), 4.17 (1H, multiplet, $C_6$ proton of naloxone), 3.86 (2H, multiplet, protons of MEM), 3.54 (2H, triplet, protons of MEM), 3.36 (3H, singlet, protons of MEM), 1.26-3.12 (14H, multiplet, protons of naloxone).

Each of: the reaction conversion (i.e., conversion from the ketone to the hydroxyl); the percentage of α epimers in the composition; and the percentage of β epimers in the composition were determined by proton NMR. $C_5$ proton of naloxone showed a singlet at 4.67 ppm in $CDCl_3$ (TMS as a reference) for 3-MEM-O-Naloxone, a doublet at 4.61 ppm (J=4.9 Hz) for α-6-HO-3-MEM-O-Naloxol and a doublet at 4.47 ppm (J=5.8 Hz) for β-6-HO-3-MEM-O-Naloxol.

The described synthesis in this Example 1 was carried out several times, and in some instances, the temperature was raised from −78° C. to 30° C. In all cases, the yield (i.e., conversion of ketone to hydroxyl) was 85% or greater and the product was always greater than 99% α-6-OH-3-MEM-O-naloxol.

Example 2

Preparation of Substantially Pure
α-6-OH-3-MEM-O-Naloxol Using
Na-tri-sec-butylborohydride

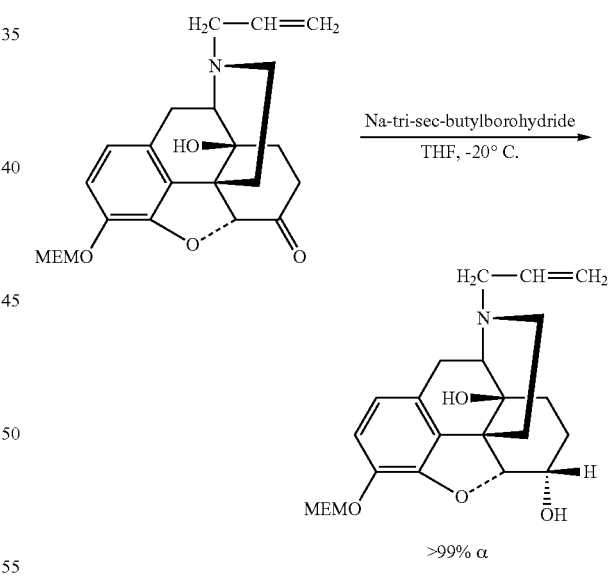

>99% α

To a solution of 3-MEM-O-naloxone base (100 mg, 0.24 mmol, preparation described in U.S. Patent Application Publication No. 2005/0136031) in dry tetrahydrofuran (8 mL) under an inert atmosphere at −20° C., was added a 1M solution of sodium tri-sec-butylborohydride (0.36 mL, 0.36 mmol) slowly. The solution was stirred continuously at −20° C. under a nitrogen atmosphere for an additional 1.0 hour and then water (1 mL) was added slowly. The reaction mixture was stirred another 10 minutes at −20° C. and allowed to warm to room temperature. The solvent was removed under reduced pressure and the remaining residue was dissolved in CH₂Cl₂ (30 mL). The CH₂Cl₂ phase was extracted with a 0.1 N HCl/NaCl water solution (3×30 mL) and the combined aqueous extracts were washed with CH₂Cl₂ (1×30 mL). Sodium carbonate was added to bring the aqueous solution to pH=8. The solution was extracted once again with CH₂Cl₂ (3×30 mL) and the organic extracts were combined, dried over anhydrous Na₂SO₄, filtered, the solvent removed under reduced pressure, and the resulting residue dried overnight in vacuo. The desired product was obtained as a colorless viscous liquid (82 mg, 0.20 mmol, 82% isolated yield). ¹H NMR (CDCl₃) showed that the desired product was greater than 99% α-6-OH-3-MEM-O-naloxol, no β epimer was detected.

The described synthesis in this Example 2 was carried out several times, and in some instances, the temperature was raised from −20° C. to 30° C. In all cases, the yield (i.e., conversion of ketone to hydroxyl) was 82% or greater and the product was always greater than 99% α-6-OH-3-MEM-O-naloxol.

Example 3

Preparation of Substantially Pure
α-6-OH-3-MEM-O-Naloxol Using Sodium
Triethylborohydride

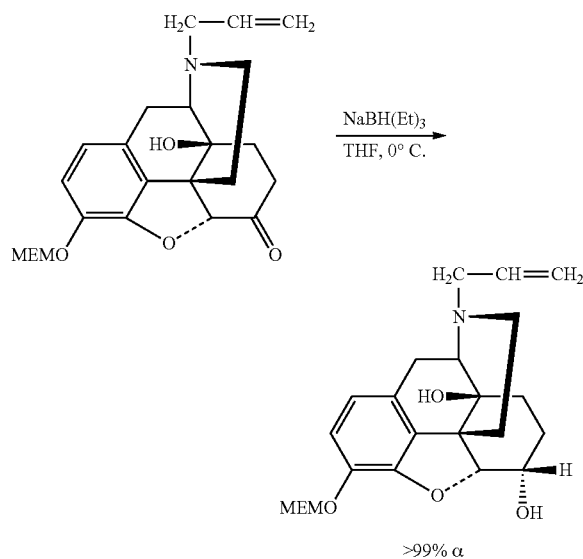

To a solution of 3-MEM-O-naloxone base (100 mg, 0.24 mmol, preparation described in U.S. Patent Application Publication No. 2005/0136031) in dry tetrahydrofuran (6 mL) under an inert atmosphere at 0° C. (via an ice bath), was added a 1M solution of sodium triethylborohydride (0.36 mL, 0.36 mmol) slowly. The solution was stirred under a nitrogen atmosphere for 5.0 hours and slowly warmed to room temperature; then acetic acid (0.5 mL) was added slowly to destroy excess sodium triethylborohydride. The solvent was removed under reduced pressure and the remaining residue was dissolved in CH₂Cl₂ (30 mL). The CH₂Cl₂ phase was extracted with a 0.1 N HCl/NaCl water solution (3×30 mL) and the combined aqueous extracts were washed with CH₂Cl₂ (1×30 mL). Sodium carbonate was added to bring the aqueous solution to pH=8. The solution was extracted once again with CH₂Cl₂ (3×30 mL) and the organic extracts were combined, dried over anhydrous Na₂SO₄, filtered, the solvent removed under reduced pressure, and the resulting residue dried overnight in vacuo. The desired product was obtained as a colorless viscous liquid (89 mg, 0.21 mmol, 89% isolated yield). ¹H NMR (CDCl₃) showed that the desired product was greater than 99% α-6-OH-3-MEM-O-naloxol, no β epimer was detected.

The described synthesis in this Example 3 was carried out several times, and in some instances, the temperature was raised from −20° C. to 30° C. In all cases, the yield (i.e., conversion of ketone to hydroxyl) was 85% or greater and the product was always greater than 99% α-6-OH-3-MEM-O-naloxol.

Example 4

Preparation of Substantially Pure
α-6-OH-3-MEM-O-Naloxol Using Sodium
Triacetoxyborohydride

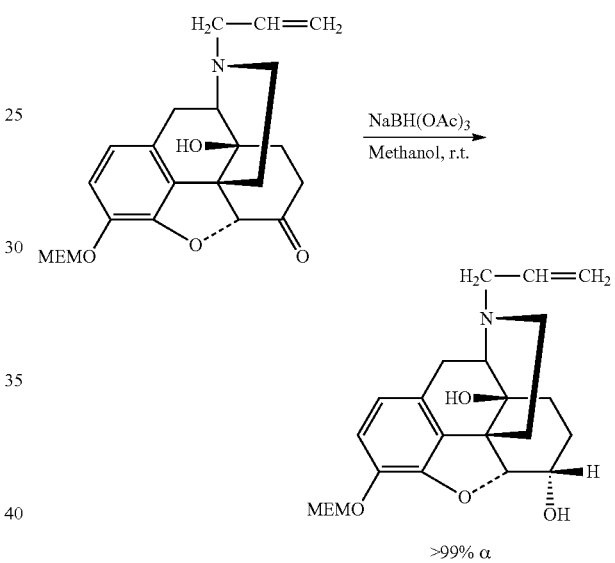

To a solution of 3-MEM-O-naloxone base (100 mg, 0.24 mmol, preparation described in U.S. Patent Application Publication No 2005/0136031) in anhydrous methanol (10 mL) under an inert atmosphere at room temperature, was added sodium triacetoxyborohydride (77 mg, 0.36 mmol) and acetic acid (15 mg, 0.24 mmol). The solution was stirred at room temperature under a nitrogen atmosphere for 5.0 hours; 2N HCl methanol solution (0.5 mL) was added slowly and the reaction solution was stirred for another 5 min. The reaction mixture was adjusted to PH=8 by addition of sodium carbonate aqueous solution. All solvents were removed under reduced pressure and the remaining residue was dissolved in CH₂Cl₂ (30 mL). The CH₂Cl₂ phase was extracted with a 0.1 N HCl/NaCl water solution (3×30 mL) and the combined aqueous extracts were washed with CH₂Cl₂ (1×30 mL). Sodium carbonate was added to bring the aqueous solution to pH=8. The solution was extracted once again with CH₂Cl₂ (3×30 mL) and the organic extracts were combined, dried over anhydrous Na₂SO₄, filtered, the solvent removed under reduced pressure, and the resulting residue dried overnight in vacuo. The product was obtained as a colorless viscous liquid. ¹H NMR (CDCl₃) showed that greater than 99% α-6-OH-3-MEM-O-naloxol was obtained in about 80% conversion, no β epimer was detected.

The described synthesis in this Example 4 was carried out several times, and in different solvents such as tetrahydrofuran, ethanol and acetonitrile, and in some instances, the temperature was raised from −20° C. to 30° C. In all cases, the conversion (i.e., conversion of ketone to hydroxyl) was 43% or greater and the product was always greater than 99% α-6-OH-3-MEM-O-naloxol.

Example 5

Comparative Study

Several reducing agents were used to reduce the ketone in the reaction schematically shown below.

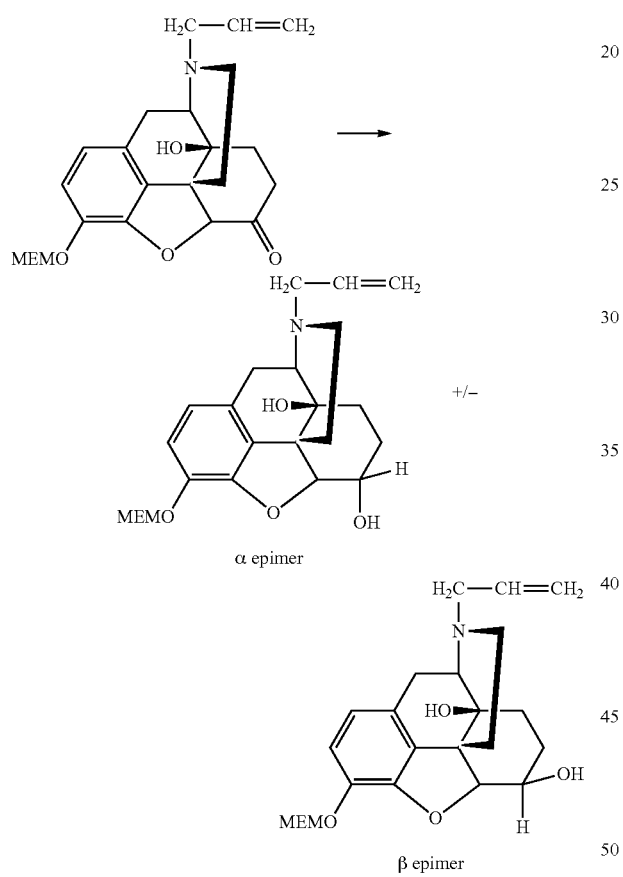
α epimer

+/−

β epimer

The structures of the reducing agents that were tested is provided below:

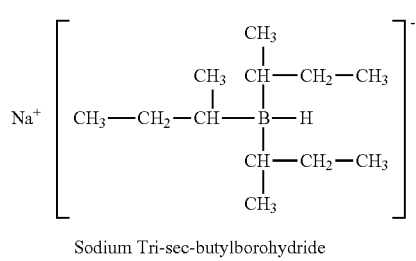
Sodium Tri-sec-butylborohydride

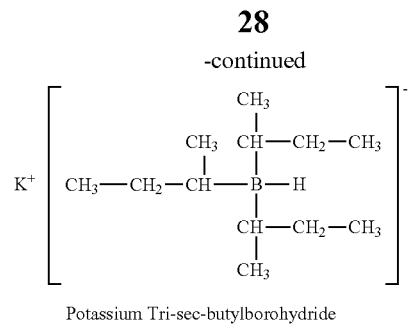
Potassium Tri-sec-butylborohydride

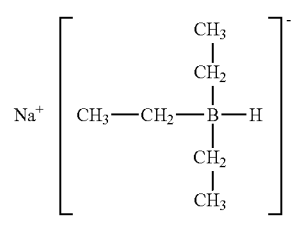
Sodium Triethylborohydride

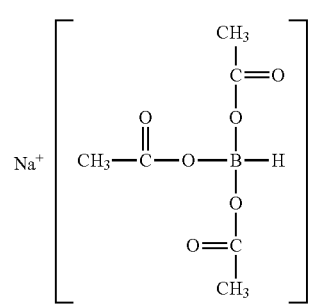
Sodium Triacetoxyborohydride

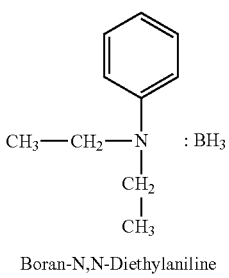
Boran-N,N-Diethylaniline

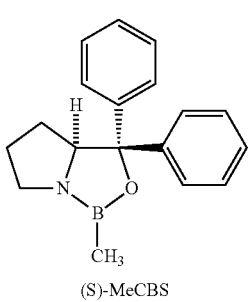
(S)-MeCBS

Each of: the reaction conversion (i.e., conversion from the ketone to the hydroxyl); the percentage of α epimers in the composition; and the percentage of β epimers in the composition were determined by proton NMR. $C_5$ proton of naloxone showed a singlet at 4.67 ppm in $CDCl_3$ (TMS as a reference) for 3-MEM-O-Naloxone, a doublet at 4.61 ppm (J=4.9 Hz) for α-6-HO-3-MEM-O-Naloxol and a doublet at 4.47 ppm (J=5.8 Hz) for β-6-HO-3-MEM-O-Naloxol.

As shown in Table 1, borane diethylaniline and sodium borohydride which do not have bulky groups, produced both α-6-HO-3-MEM-O-Naloxol and β-6-HO-3-MEM-O-Naloxol with α epimer as the major product relative to the β epimer. The reaction conversion of sodium borohydride (~92%) was much higher than that of borane diethylaniline (~29%). The conversion amount, however, was relatively low for both reducing agents. Even for sodium borohydride, the amount of conversion to the α epimer was less than 65% on a molar basis (about 92% conversion*about 68% α epimer).

TABLE 1

Stereoselective Reduction of 3-MEM-O-Naloxone by Borane and Borohydride

| Reducing Reagent | Reaction Conditions | Conversion (%) | α epimer (%) | β epimer (%) |
| --- | --- | --- | --- | --- |
| $NaBH_4$ | 1.5 eqv $NaBH_4$, methanol, −20° C. to room temperature. overnight. | ~92% | ~68% | ~24% |
| Borane Diethylaniline | 1.5 eqv Borane Diethylaniline, THF, 0° C. to room temperature. 18 hours | ~29% | ~22% | ~7% |

It was found that all sodium trialkylborohydrides produced exclusively α-6-HO-3-MEM-O-Naloxol in almost quantitive yields (within the means of detection), without any detectable β epimer. See Table 2. It made no difference that the reaction was carried out at −78° C., −20° C. or 0° C., and the reaction generally completed in a few hours. Will not wishing to be bound by theory, the three bulky groups associated with these reducing reagents resulted in steric effects such that the reagent could only approach from a relatively open side of the ketone-containing structure, thereby producing only α epimer. Further, the electron-donating properties of alkyl groups are theorized to make the corresponding borohydride more active, thereby resulting in high yields. The sodium trialkyl borohydrides can be easily destroyed by water or acetic acid. Sodium trialkylborohydrides appear to be preferred in terms of selectivity and reactivity.

TABLE 2

Stereoselective Reduction of 3-MEM-O-Naloxone by Sodium Trialkylborohydrides

| Reducing Reagent | Reaction Temp. | Reaction Conditions | Conversion (%) | α epimer (%) | β epimer (%) |
| --- | --- | --- | --- | --- | --- |
| Potassium Tri-sec-butylborohydride | −78° C. to room temperature. | 1.5 eqv Potassium Tri-sec-butylborohydride, THF, 1.0 hour. | ~99% | 100% | 0% |
| Potassium Tri-sec-butylborohydride | −20° C. to room temperature. | 1.5 eqv Potassium Tri-sec-butylborohydride, THF, 1.0 hour. | ~99% | 100% | 0% |
| Potassium Tri-sec-butylborohydride | 0° C. to room temperature. | 1.5 eqv Potassium Tri-sec-butylborohydride, THF, 1.0 hour. | ~99% | 100% | 0% |
| Sodium Tri-sec-butylborohydride | −20° C. to room temperature. | 1.5 eqv Sodium Tri-sec-butylborohydride, THF, 1.0 hour. | ~99% | 100% | 0% |
| $NaBH(Et)_3$ | 0° C. to room temperature. | 1.5 eqv $NaBH(Et)_3$, THF, 5.0 hours. | ~99% | 100% | 0% |

Sodium triacetoxyborohydride was a mild stereoselective reducing agent. It was solid and much less sensitive to moisture and air than sodium trialkylborohydride. The reduction results by sodium triacetoxyborohydride in different solvents and reaction conditions are listed in Table 3.

Except the reduction in THF in which ~1% β epimer was found, all other reductions using sodium triacetoxyborohydride gave 100% α-6-HO-3-MEM-O-Naloxol without any detectable β epimer. Again, while not wishing to be bound by theory, it is believed that the three acetoxy groups of sodium triacetoxyborohydride are bulky enough to force borohydride to selectively attack the ketone group. However, the reaction conversions were not ideal and influenced by solvents in the order of methanol>THF>acetonitrile. As seen in the third row of Table 3, irradiation did not appear to improve the percent of conversion.

TABLE 3

Stereoselective Reduction of 3-MEM-O-Naloxone by Sodium Triacetoxyborohydride

| Reducing Reagent | Solvent | Reaction Conditions | Conversion (%) | α epimer (%) | β epimer (%) |
|---|---|---|---|---|---|
| NaBH(OAc)$_3$ | Methanol | 1.5 eqv NaBH(OAc)$_3$, 1 eqv HOAc, room temperature. 5.0 hours. | ~80% | 100% | 0% |
| NaBH(OAc)$_3$ | THF | 1.5 eqv NaBH(OAc)$_3$,, −20° C. to room temperatuer 4.0 hours. | ~60% | ~99% | ~1% |
| NaBH(OAc)$_3$ | Ethanol | 1.5 eqv NaBH(OAc)$_3$, 1 eqv HOAc, microwave 60° C., 15 minutes. | ~43% | 100% | 0% |
| NaBH(OAc)$_3$ | CH$_3$CN | 1.5 eqv NaBH(OAc)$_3$, 5 eqv HOAc, room temperature. 6.0 hours. | ~47% | 100% | 0% |

The reduction of 3-MEM-O-Naloxone was also tested by using enantioselective catalyst (S)-MeCBS and sodium triethylborohydride in the presence of a borane source. See Table 4. Neither reaction gave the desired results. Proton NMR showed that some side products were formed when borane/NaBH(Et)$_3$ was used. See second row of Table 4.

TABLE 4

Catalytic Stereoselective Reduction of 3-MEM-O-Naloxone

| Reductive Reagent | Reaction Conditions | Conversion (%) | α epimer (%) | β epimer (%) |
|---|---|---|---|---|
| Borane Diethylaniline and (S)-MeCBS | 1.5 eqv Borane Diethylaniline, 5% (S)-MeCBS THF, room temperature. 18 hours | ~62% | ~43% | ~19% |
| Borane THF and NaBH(Et)$_3$ | 1.0 eqv Borane THF, 10% NaBH(Et)$_3$, THF, room temperature. 5 hours | 0 | 0 | 0 |

What is claimed is:

1. A synthetic method comprising:
stereoselectively reducing a ketone of a morphinone to a hydroxyl using a reducing agent selected from the group consisting of potassium tri-sec-butylborohydride and sodium tri-sec-butylborohydride to form a reduced morphinone, wherein the morphinone and the reduced morphinone have the following structures:

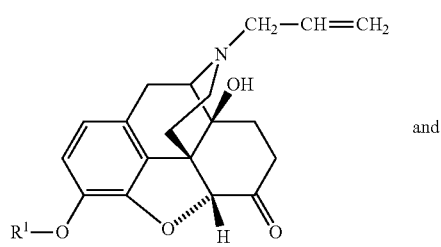

and

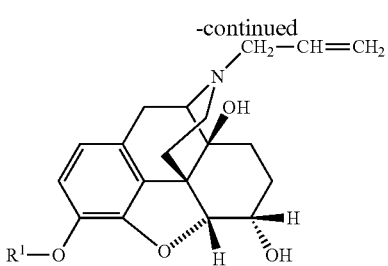

respectively, wherein R$^1$ is H or a hydroxyl protecting group; and wherein the synthetic method has a conversion yield of 85% or greater of the ketone to the hydroxyl, and 99% or greater of the reduced morphinone is in an α epimer form.

2. The method of claim 1, wherein R$^1$ is H.

3. The method of claim 1, wherein R$^1$ is a hydroxyl protecting group selected from the group consisting of alkanoyl having 2 to 5 carbons; aryloyl having 7 to 11 carbons, benzyl, 1 ethoxyethyl, methoxymethyl, 4-methoxyphenylmethyl, methoxyethoxymethyl, 1 ethoxyethyl, benzyloxymethyl, (β trimethylsilylethoxy)methyl, tetrahydropyranyl, 2,2,2 trichloroethoxycarbonyl, t butyl(diphenyl)silyl, trialkylsilyl, trichloromethoxycarbonyl and 2,2,2-trichloroethoxymethyl.

4. The method of claim 3, wherein R$^1$ is methoxyethoxymethyl.

5. The method of claim 1, wherein the conversion yield is at least 95%.

6. The method of claim 5, wherein the conversion yield is at least 98%.

7. The method of claim 1, wherein the stereoselective reduction is performed in a solvent of tetrahydrofuran.

8. The method of claim 1, wherein the reducing agent is potassium tri-sec-butylborohydride.

* * * * *